United States Patent [19]

Single

[11] Patent Number: 5,941,905
[45] Date of Patent: Aug. 24, 1999

[54] PUBLIC ALARM FOR COCHLEAR IMPLANT

[75] Inventor: Peter Single, Lane Cove, Australia

[73] Assignee: Cochlear Limited, Lane Cove, Australia

[21] Appl. No.: 09/012,909

[22] Filed: Jan. 23, 1998

[51] Int. Cl.[6] ....................................... A61N 1/08
[52] U.S. Cl. ............................. 607/57; 607/63
[58] Field of Search ................... 607/31, 32, 55, 607/56, 57, 60, 63, 136, 137; 128/903

[56] References Cited

U.S. PATENT DOCUMENTS

| | | |
|---|---|---|
| 4,532,930 | 8/1985 | Crosby et al. . |
| 4,793,353 | 12/1988 | Borkan ...................................... 607/57 |
| 5,314,453 | 5/1994 | Jeutter ....................................... 607/60 |
| 5,486,814 | 1/1996 | Quinones . |
| 5,584,869 | 12/1996 | Heck et al. ............................... 607/57 |

FOREIGN PATENT DOCUMENTS

| | | |
|---|---|---|
| 0581416 | 2/1994 | European Pat. Off. . |
| 9600558 | 6/1996 | WIPO . |

*Primary Examiner*—William E. Kamm
*Assistant Examiner*—George R. Evanisko
*Attorney, Agent, or Firm*—Gottlieb, Rackman & Reisman, P.C.

[57] ABSTRACT

A monitor for a therapeutic device such as a cochlear implant monitors the leakage RF signals between the external and the internal components. In one embodiment, absence of RF signals is interpreted by the monitor as being indicative of either an out-of-range condition or a flat battery condition and a sound and/or visual signal is generated to indicate this condition to an attendant. In a more complex embodiment, special indication signals either are superimposed on the standard signals and used to uniquely identify the cochlear implant or to provide an indication of certain preselected features of the external component. The monitor is especially useful for infant cochlear implants.

13 Claims, 3 Drawing Sheets

PUBLIC ALARM FOR COCHLEAR IMPLANT

BACKGROUND OF THE INVENTION

A. Field of the Invention

This invention pertains to an apparatus for providing an alarm indicative of a condition of a wearable therapeutic device, such as, for example, a cochlear implant system, as well as to a method related to said apparatus.

B. Description of the Prior Art

Various devices, such as cochlear implants, are being used to assist persons having a chronic aural disability or impairment which cannot be alleviated by external hearing aids. These devices typically include two sections: an external section and an internal section which is implanted into the patient. The external section typically includes a microphone for converting ambient sounds into electrical signals, signal processing means for converting the electrical signals into processed signals, and a signal transmitter for transmitting the processed signals to the internal section. In turn, the internal section includes receiver means for receiving signals from the transmitter, signal processor means for processing the received signals, and stimulating means for stimulating the inner ear of the person, such as the cochlea, in accordance with the received signals. The external section further includes various manual controls for the operation of the device, such as a volume control, battery checking, and so on.

It has been found that for best results, cochlear implant devices should be provided to a patient at the earliest possible age. A problem however occurs if the patient is a small, immature infant. More specifically, with most patients, if the device stops functioning, for example due to a low battery, or a malfunction, the patient can indicate this to a nurse, spouse or other attendant. However, an infant who is essentially deaf and is unable to communicate cannot indicate to anyone that there is a problem, especially since he may be too young to even recognize that there was a problem in the first place.

OBJECTIVES AND SUMMARY OF THE INVENTION

In view of the above-mentioned disadvantages, it is an objective of the present invention to provide a system or apparatus which automatically monitors a cochlear device, and provides either an audible or visual indication to an attendant in case of a problem.

A further objective is to provide a system which can be used easily by a person, without any special instructions or extensive learning period.

Yet a further objective is to provide a device which can be made easily and inexpensively without the need for expensive additional parts or extensive changes in existing product lines.

A further objective is to provide an indicating method and apparatus which can be readily used with existing cochlear devices without any modifications.

Other objectives and advantages of the invention shall become apparent from the following description. Briefly, a device for aiding a hearing impaired person constructed in accordance with this invention includes an external section having a microphone for receiving ambient sounds and converting the same into electrical signals, signal processing means for converting the signals and a transmitter for sending the converted signals to an internal section through an inductive coupling. This coupling is normally associated with, or produces as a by-product, a radio frequency (RF) signal. Importantly, the present invention further contemplates a third, monitoring section adapted to receive and sense said RF signal, and to generate an audible or visual indication via an appropriate annunciator as to whether said RF signal is sensed or not. This third section is normally worn on a clothing article or pocket by an attendant including a parent, a nurse, or other attendant, so that the latter can determine easily whether the cochlear implant device is operating properly.

DETAILED DESCRIPTION OF THE INVENTION

Figure 1:
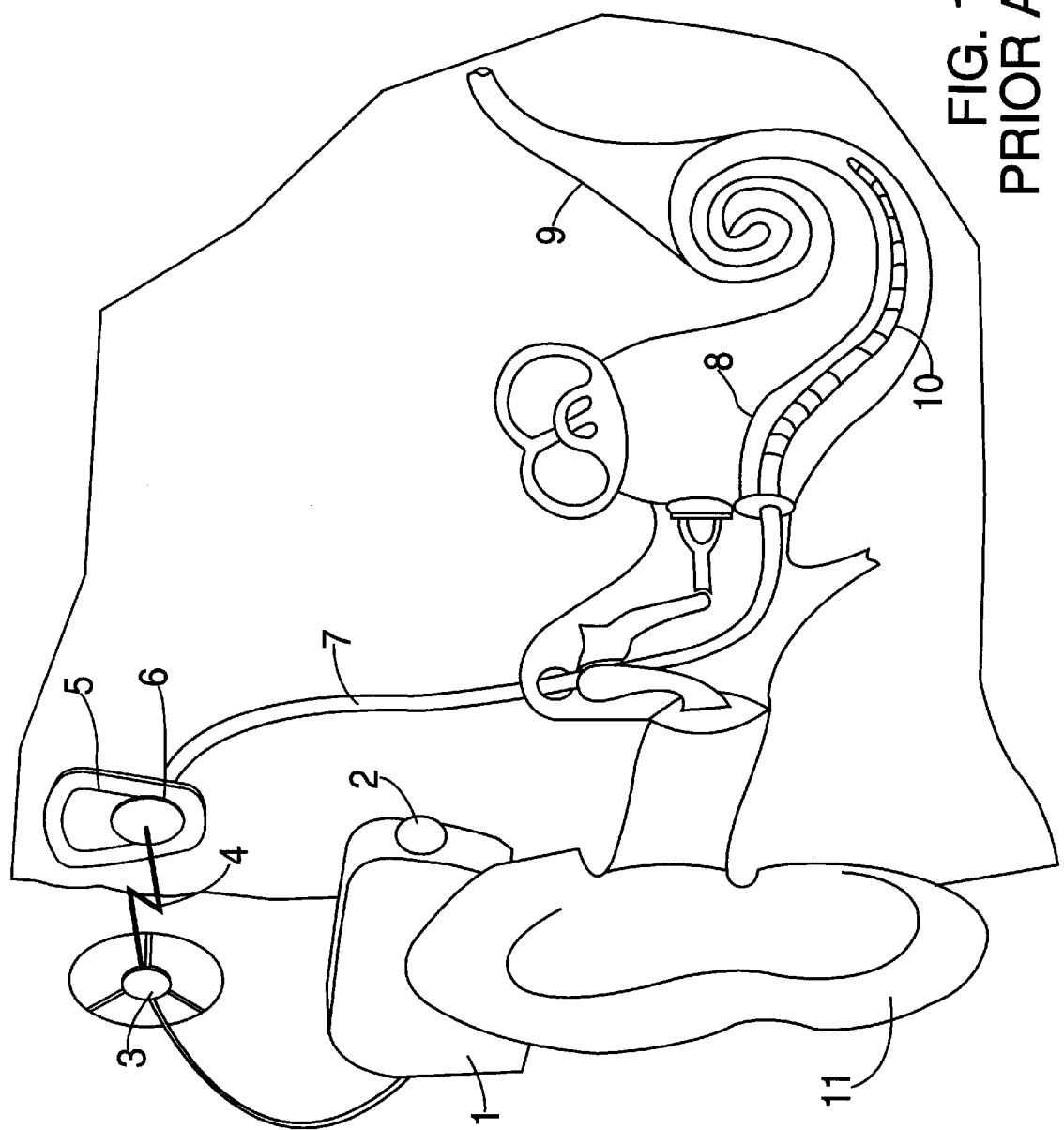
FIG. 1 shows a standard prior art cochlear implant device.

Referring now to the drawings, and more particularly to FIG. 1, a typical cochlear implant device consists of an external section which is essentially a speech processor 1. The external section 1 includes a microphone 2.

The speech processor 1 is constructed and arranged so that it can fit behind the outer ear 11. Alternatively, it can be worn on the body.

Attached to speech processor 1 is a transmitter coil 3 which transmits the electrical signals to the internal section via an RF link 4.

The internal or implanted section includes a receive coil for receiving the electrical signals from the coil 3, i.e. RF signals 4. Attached to the receiver coil 5 is the implanted receiver 6. A cable 7 extends from the receiver 6 to the cochlea 8 and terminates in an electrode array 10. The signals thus received are applied by the array 8 to the auditory nerve 9. The operation of the device shown in FIG. 1 is described for example in U.S. Pat. No. 4,532,930.

Figure 2:
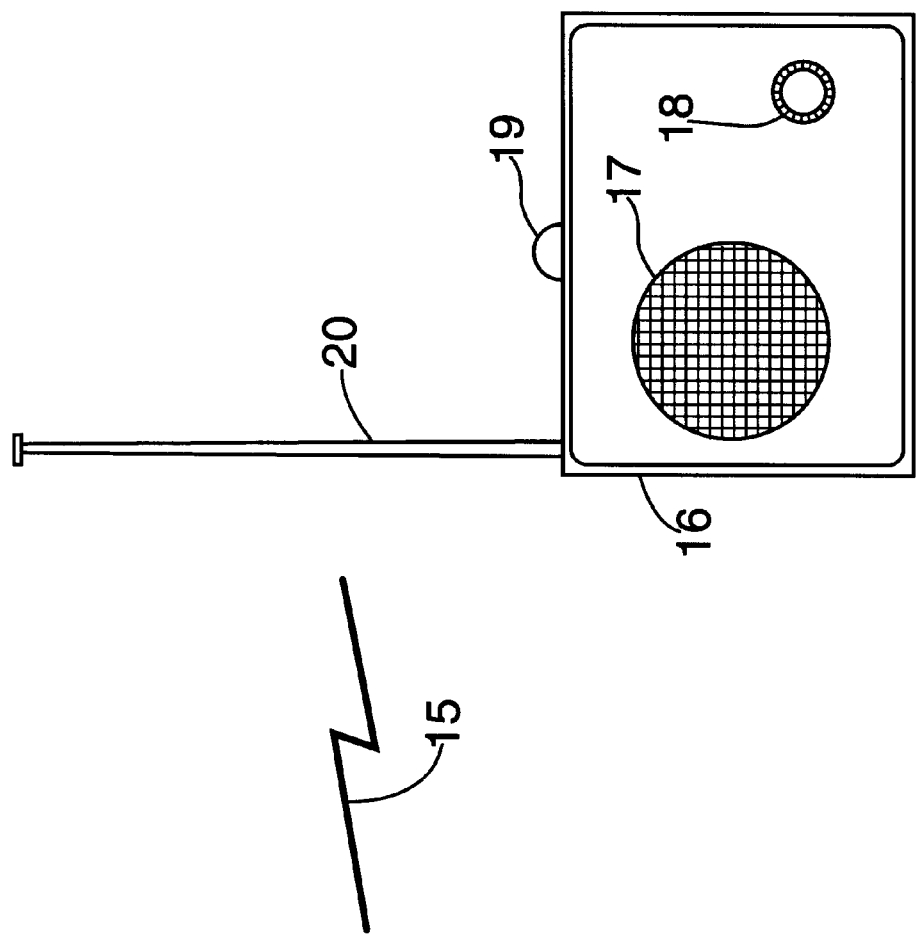
FIG. 2 shows a monitoring section used to monitor a cochlear implant device such as the one shown in FIG. 1.
Figure 2:
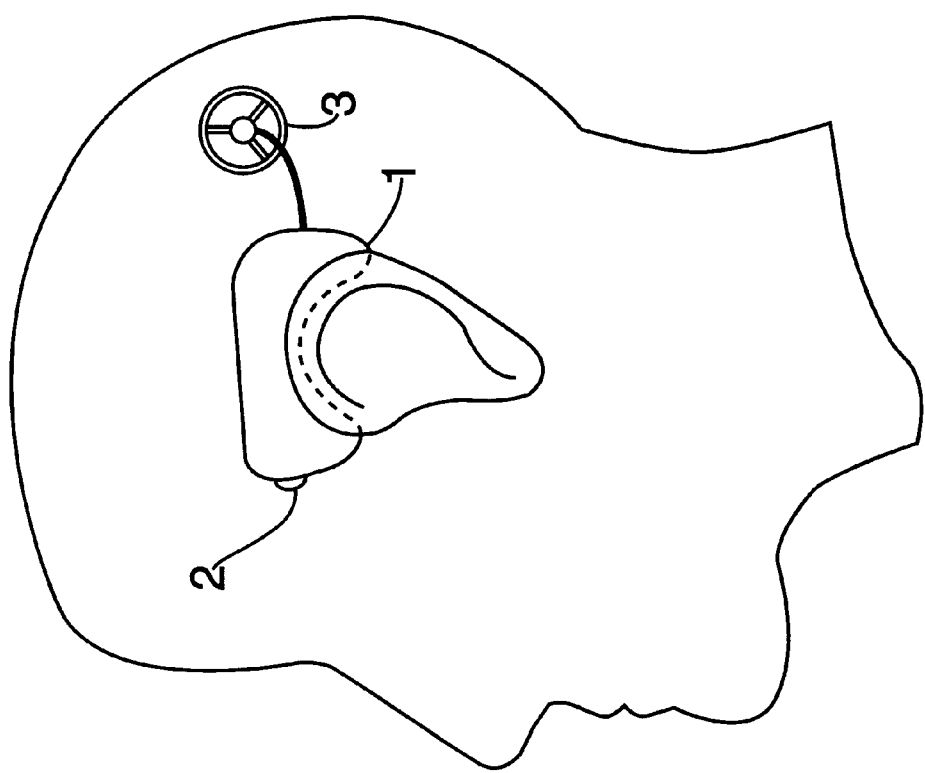

Referring now to FIG. 2, the subject device further includes a monitor 16. The device includes a speaker 17 and/or an indicator alarm light 19. The monitor is further provided with an on/off-volume controller 18 and an antenna 20.

The invention operates as follows. Under normal conditions, the microphone 2 picks up ambient sounds and converts them into corresponding electrical signals. The speech processor 1 senses these sounds and translates them into corresponding cochlear excitation signals. The excitation signals are then transmitted to the implanted section via channel 4. The receiver 6 receives these signals and after suitable translation (if necessary) applies them to the auditory nerve 9 through array 10. Preferably the RF signals are transmitted by an inductive coupling between the coils 3 and 5.

Importantly, not all the energy of the RF waves 4 are intercepted by receiver 5. Instead some of the energy leaks away, as indicated in FIG. 2 at 15. The monitor 16 is arranged and constructed so that it receives and senses this leakage and uses it as a confirmation signal that the cochlear device operates satisfactorily.

The simplest method of implementing the invention is to make monitor 16 a simple radio receiver for receiving the leakage signal 15. The monitor then decides whether the signal 15 is sensed or not. If no signal is sensed, then a sound is emitted by speaker 17 to indicate that either the cochlear implant device is out of range or it has ceased functioning properly. The volume of the sound is controlled by volume controller 18. Alternatively, or in addition, alarm lamp 19 is turned on for the same purpose. The monitor 16 is carried by a parent, guardian, nurse or other attendant associated with the patient.

Figure 3:
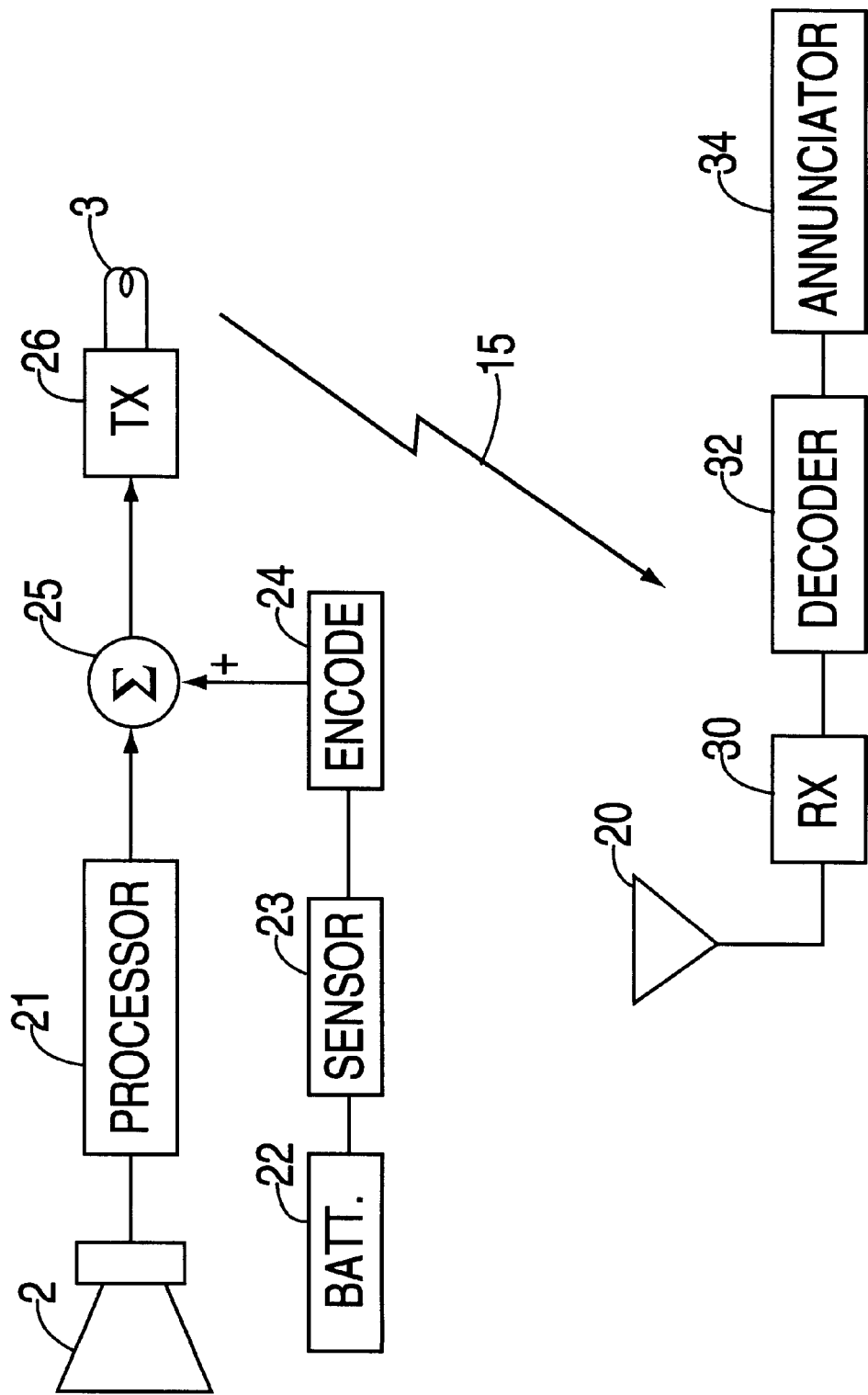
FIG. 3 shows an alternate embodiment of the invention.

In more complex implementations, the speech processor may use an encoder to provide a low battery indication. More particularly, as shown in FIG. 3, the speech processor 1 may include a signal processor 21 which receives the electrical signals from microphone 2. The speech processor 1 further includes a battery 22 which provided power to both the speech processor and the internal section.

The condition of the battery 22 is sensed by a sensor 23. The sensor 23 generates an appropriate signal to encoder 24 which generates a battery condition signal. This signal is added to the signal from signal processor 21 by summer 25. The sum is transmitted by transmitter 26 to coil 3.

Leakage 15 is now detected by receiver 30 through the antenna 20. The received signal is decoded by decoder 32 and a signal corresponding to the component of the received signal indicative of the battery condition is fed to an annunciator 34 which may consists of either the speaker 17 or lamp 19. The annunciator 32 is activated if the battery condition indicator signal indicates that the battery 22 is flat.

In this case, the monitor 16 may distinguish between a flat battery condition and the infant being out of range since in the first instance the battery condition signal is present, while in the second instance no signal is sensed at all. Another advantage of the second embodiment is that the signal from encoder 24 may include a serial number or other signals uniquely identifying the speech processor 1. In this manner, several infants may be located in a common area, for example a class room, each student wearing a special speech processor as described in FIG. 3 and the attendant having either a monitor for each student or a combined monitor adapted to monitor several students. Of course a disadvantage of this embodiment is that it requires more parts, and in addition the speech processor has to be redesigned to include the battery sensor 23, encoder 24 and summer 25.

The monitor 16 may perform more complicated functions as well, such as determining if the signals from the speech processor 1 are appropriate for the implant, or whether other functions are performed properly by the speech processor Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

I claim:

1. A device for aiding a person having a hearing impairment, said device comprising:
   an external component including a microphone for converting ambient sounds into electrical signals; a signal processor connected to said microphone for processing said electrical signals into stimulation signals; and a transmitter coupled to said signal processor for transmitting RF signals corresponding to said stimulation signals;
   an internal component including an internal receiver for receiving said RF signals, said internal component for applying pulses to an auditory nerve of said person corresponding to said stimulation signals; and
   a monitor separate from said internal component and having a monitor receiver receiving said RF signals, said monitor generating an output corresponding to said RF signals.

2. The device of claim 1 wherein said monitor includes an annunciator activated in accordance with said RF signals.

3. The device of claim 2 wherein said annunciator is activated in the absence of said RF signals.

4. The device of claim 2 wherein said annunciator is a speaker.

5. The device of claim 2 wherein said annunciator is a lamp.

6. The device of claim 1 wherein the transmitter also transmits the RF signal corresponding to the battery condition and wherein said external component includes a battery having a normal and a flat condition, and wherein said output is generated to indicate said flat condition.

7. The device of claim 6 wherein said external component includes an encoder for generating an indication signal indicative of a preselected condition and a summer for summing said stimulation signal and said indication signal to generate a combined signal, said transmitter transmitting said RF signals corresponding to said combined signal.

8. The device of claim 7 wherein said monitor includes a decoder for decoding said indication signal from said external portion.

9. The device of claim 8 wherein said encoder generates a signal including an identifier uniquely identifying said external component and wherein said monitor includes a decoder for recognizing said identifier.

10. The device of claim 7 where said indication signal is indicative of a battery condition.

11. A device for aiding a person having a hearing impairment, said device comprising:
    an external component including a microphone for converting ambient sounds into electrical signals; a signal processor connected to said microphone for processing said electrical signals into stimulation signals; a transmitter coupled to said signal processor for transmitting RF signals corresponding to said stimulation signals; and a battery powering said external component, said battery having a battery condition including a normal condition and a flat condition;
    an internal component including an internal receiver for receiving said RF signals, said internal component for applying pulses to an auditory nerve of said person corresponding to said stimulation signals; and
    a monitor separate from said internal component and having a monitor receiver receiving said RF signals, said monitor generating an output based on said RF signals, said output being indicative of said battery condition.

12. A device for aiding a person having a hearing impairment, said device comprising:
    an external component including a microphone for converting ambient sounds into electrical signals; a signal processor connected to said microphone for processing said electrical signals into stimulation signals; an encoder generating a unique identifier associated with said external component to uniquely identify the same; and a transmitter coupled to said signal processor for transmitting RF signals corresponding to said stimulation signals and said identifier;
    an internal component including an internal receiver for receiving said RF signals, said internal component for applying pulses to an auditory nerve of said person corresponding to said stimulation signals; and a monitor separate from said internal component and having a monitor receiver receiving said RF signals from said external component, said monitor including an annunciator generating an output based on said RF signals received from said external component and a decoder for decoding said identifier for recognizing said identifier.

13. A device for aiding a person having a hearing impairment, said device comprising:

an external component including a microphone for converting ambient sounds into electrical signals; a signal processor connected to said microphone for processing said electrical signals into stimulation signals; an encoder generating a unique identifier associated with said external component to uniquely identify the same; a battery powering said external component, said battery having a battery condition including a normal condition and a flat condition; and a transmitter coupled to said signal processor for transmitting RF signals corresponding to said stimulation signals, said identifier, and said battery condition;

an internal component including an internal receiver for receiving said RF signals, said internal component for applying pulses to an auditory nerve of said person corresponding to said stimulation signals; and a monitor separate from said internal component and having a monitor receiver receiving said RF signals, said monitor generating an output based on said RF signals, said output being indicative of said battery condition; said monitor including a decoder for decoding said identifier for recognizing said identifier.

* * * * *